United States Patent
Christ et al.

(10) Patent No.: US 9,968,705 B2
(45) Date of Patent: May 15, 2018

(54) BIOSCAFFOLDS FOR FORMATION OF MOTOR ENDPLATES AND OTHER SPECIALIZED TISSUE STRUCTURES

(71) Applicant: Wake Forest University Health Sciences, Winston-Salem, NC (US)

(72) Inventors: George J. Christ, Lewisville, NC (US); Justin M. Saul, Oxford, OH (US); John B Scott, Winston-Salem, NC (US); Benjamin T. Corona, Converse, TX (US); Benjamin S. Harrison, Tobaccoville, NC (US); Catherine Ward, San Antonio, TX (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 211 days.

(21) Appl. No.: 14/348,273

(22) PCT Filed: Sep. 28, 2012

(86) PCT No.: PCT/US2012/057904
§ 371 (c)(1),
(2) Date: Mar. 28, 2014

(87) PCT Pub. No.: WO2013/049563
PCT Pub. Date: Apr. 4, 2013

(65) Prior Publication Data
US 2014/0234388 A1   Aug. 21, 2014

Related U.S. Application Data (60) Provisional application No. 61/541,652, filed on Sep. 30, 2011.

(51) Int. Cl.
*A61L 27/22*     (2006.01)
*A61K 31/27*     (2006.01)
(Continued)

(52) U.S. Cl.
CPC ............ *A61L 27/227* (2013.01); *A61K 31/27* (2013.01); *A61K 31/341* (2013.01);
(Continued)

(58) Field of Classification Search
CPC .... A61L 27/3873; A61L 27/446; A61L 27/48; A61L 27/52; A61L 27/54; A61L 27/58;
(Continued)

(56) References Cited

U.S. PATENT DOCUMENTS 5,573,784 A    11/1996  Badylak et al.
6,051,750 A    4/2000   Bell
(Continued)

FOREIGN PATENT DOCUMENTS

WO     WO 2012/021814 A2     2/2012

OTHER PUBLICATIONS

Bezadova et al., Muscle Activity and Muscle Agrin Regulate the Organization of Cytoskeletal Proteins and Attached Acetylcholine Receptor (AChR) Aggregates in Skeletal Muscle Fibers, The Journal of Cell Biology (Jun. 25, 2001) 153 (7): 1453-1463. (Year: 2001).*

(Continued)

*Primary Examiner* — Ernst V Arnold
*Assistant Examiner* — Miriam A Levin
(74) *Attorney, Agent, or Firm* — Myers Bigel, P.A.

(57) ABSTRACT

Provided herein are scaffolds and methods useful to promote the formation of functional clusters on a tissue, for example, motor endplates (MEPs) or a component thereof on skeletal muscle cells or tissue, as well as the use of scaffolds so produced for repairing a tissue injury or defect.

12 Claims, 4 Drawing Sheets

(51) Int. Cl.

| | | |
|---|---|---|
| *A61K 31/341* | (2006.01) | |
| *A61K 31/465* | (2006.01) | |
| *A61L 27/38* | (2006.01) | |
| *A61L 27/44* | (2006.01) | |
| *A61L 27/48* | (2006.01) | |
| *A61L 27/52* | (2006.01) | |
| *A61L 27/54* | (2006.01) | |
| *A61L 27/58* | (2006.01) | |
| *A61K 33/24* | (2006.01) | |
| *A61K 33/26* | (2006.01) | |
| *A61K 33/38* | (2006.01) | |
| *A61L 27/36* | (2006.01) | |
| *A61L 27/50* | (2006.01) | |
| *C12N 5/077* | (2010.01) | |
| *G01N 33/553* | (2006.01) | |
| *A61K 38/17* | (2006.01) | |

(52) U.S. Cl.
CPC ............ *A61K 31/465* (2013.01); *A61K 33/24* (2013.01); *A61K 33/26* (2013.01); *A61K 33/38* (2013.01); *A61L 27/3604* (2013.01); *A61L 27/3826* (2013.01); *A61L 27/3873* (2013.01); *A61L 27/446* (2013.01); *A61L 27/48* (2013.01); *A61L 27/50* (2013.01); *A61L 27/52* (2013.01); *A61L 27/54* (2013.01); *A61L 27/58* (2013.01); *C12N 5/0658* (2013.01); *G01N 33/553* (2013.01); *A61K 38/17* (2013.01); *A61L 2300/252* (2013.01); *A61L 2300/622* (2013.01); *A61L 2430/30* (2013.01)

(58) Field of Classification Search
CPC .... A61L 27/227; A61L 27/3604; A61L 27/50; A61L 27/3826; A61L 2300/252; A61L 2300/622; A61L 2430/30; A61L 27/225; A61K 33/24; A61K 33/26; A61K 33/38; A61K 31/27; A61K 31/341; A61K 31/465; A61K 38/17; C12N 5/0658; G01N 33/553
USPC .................. 424/93.7, 423; 264/41; 435/396
See application file for complete search history.

(56) References Cited

U.S. PATENT DOCUMENTS

| | | | |
|---|---|---|---|
| 6,206,931 B1 | 3/2001 | Cook et al. | |
| 6,214,021 B1 | 4/2001 | Hadlock et al. | |
| 6,485,723 B1 | 11/2002 | Badylak et al. | |
| 6,592,623 B1 | 7/2003 | Bowlin et al. | |
| 6,998,418 B1 | 2/2006 | Sung et al. | |
| 7,729,628 B2 | 6/2010 | Nakayama | |
| 7,972,628 B2 | 7/2011 | Ratner et al. | |
| 2005/0095298 A1 | 5/2005 | Gronlund et al. | |
| 2006/0045903 A1* | 3/2006 | Kadiyala ................. | A61F 2/08 424/426 |
| 2006/0239981 A1 | 10/2006 | Yoo et al. | |
| 2008/0193910 A1 | 8/2008 | Larkin et al. | |
| 2009/0035349 A1 | 2/2009 | Gazit et al. | |
| 2011/0183910 A1 | 7/2011 | Fallon et al. | |

OTHER PUBLICATIONS

John Bradford Scott, Development of a Tissue Engineered Skeletal Muscle Repair Construct Featuring Biomimetic Physical, Chemical and Mechanical Cues, Dissertation, Wake Forest University Graduate School of Arts and Sciences (2015), 200 pages. (Year: 2015).*
Scott et al., Achieving Acetylcholine Receptor Clustering in Tissue-Engineered Skeletal Muscle Constructs In vitro through a Materials-Directed Agrin Delivery Approach, frontiers in Pharmacology (Jan. 2017) vol. 7, Article 508, pp. 1-16 (Year: 2017).*
Supplementary Partial European Search Report, EP12835869, dated Apr. 24, 2015, 3 pages.
Daggett DF et al. The role of an agrin-growth factor interaction in ACh receptor clustering. Molecular and Cellular Neuroscience. Oct. 1, 1996; 8(4): 272-285.
Glass DJ et al. Agrin acts via a MuSK receptor complex. Cell. May 17, 1996; 85(4): 513-523.
Kim S et al. NGL family PSD-95-interacting adhesion molecules regulate excitatory synapse formation. Nature Neuroscience. Sep. 17, 2006; 9(10): 1294-1301.
Zammit PS et al. The skeletal muscle satellite cell: the stem cell that came in from the cold. Journal of Histochemistry & Cytochemistry. 2006; 54(11): 1177-1191.
Hurme T. Healing of skeletal muscle injury: an ultrastructural and immunohistochemical study. Sci Sports Exerc. Jul. 1991; 23(7): 801-810, Abstract only.
Campion DR. The muscle satellite cell: a review. Int Rev Cytol. 1984; 87: 225-251, Abstract only.
Linnes MP, et al. A fibrinogen-based precision microporous scaffold for tissue engineering. Biomaterials. Dec. 2007; 28(35): 5298-5306.
Stokols et al. Templated agarose scaffolds support linear axonal regeneration. Tissue Engineering. Oct. 2006; 12(10): 2777-2787, Abstract only.
Flynn L. Fiber templating of poly(2-hydroxyethyl methacrylate) for neural tissue engineering. Biomaterials. 2003; 24: 4265-4272.
Heuser JE and Reese TS. Structural changes after transmitter release at the frog neuromuscular junction. Journal of Cell Biology. Mar. 1981; 88: 564-580.
Huh K-H and Fuhrer C. Clustering of nicotinic acetylcholine receptors: from the neuromuscular junction to interneuronal synapses. Molecular Neurobiology. 2002; 25: 79-112.
Oosterhuis H et al. Myasthenia gravis and myasthenic syndromes. Curr Opin Neurol Neurosurg. Oct. 1992; 5(5):638-44, Citation only.
Corona BT et al. Further development of a tissue engineered muscle repair construct in vitro for enhanced functional recovery following implantation in vivo in a murine model of volumetric muscle loss injury. Tissue Engineering: Part A. 2012; 18(11 and 12): 1213-1228.
Ngo ST et al. Neural agrin: a synaptic stabiliser. Int J Biochem Cell Biol. 2007; 39(5): 863-7, Abstract only.
Stetefeld J et al. Modulation of agrin function by alternative splicing and Ca2+ binding. Structure. Mar. 2004; 12(3): 503-15.
Witzemann V. Development of the neuromuscular junction. Cell Tissue Res. 2006; 326: 263-271.
Kummer TT et al. Assembly of the postsynaptic membrane at the neuromuscular junction: paradigm lost. Current Opinion in Neurobiology, 20016; 16: 74-82.
Extended European Search Report and Search Opinion, EP 12835869.4, dated Sep. 10, 2015.
Meechaisue C et al. Electrospun mat of tyrosine-derived polycarbonate fibers for potential use as tissue scaffolding material. J. Biomater. Sci. Polymer Edn. Sep. 2006; 17(9): 1039-1056.
International Search Report and Written Opinion, PCT/US/2012/057904, dated Feb. 15, 2013, 9 pages.
Scott JB et al. "Achieving Acetylcholine Receptor Clustering in Tissue-Engineered Skeletal Muscle Constructs In Vitro through a Materials-Directed Agrin Delivery Approach", *Front. Pharmacol.* 7(508) 2016; 35 pages.

* cited by examiner

150 μm TEMPLATE

FIG. 5

BIOSCAFFOLDS FOR FORMATION OF MOTOR ENDPLATES AND OTHER SPECIALIZED TISSUE STRUCTURES

RELATED APPLICATIONS

This application claims the benefit of U.S. provisional application Ser. No. 61/541,652, filed Sep. 30, 2011, which is incorporated by reference herein in its entirety.

FIELD

The present disclosure concerns biomaterial constructs useful to support the delivery of agents of interest.

BACKGROUND

Muscle deficiencies due to a host of congenital or acquired conditions, including, but not limited to, surgery, inflammation, traumatic injury, and disease, can lead to the irrecoverable loss of muscle function. For those who suffer from such defects, there are currently few clinical treatments available.

Cell-based approaches have been studied to regenerate or re-create muscle tissues such as skeletal muscle de novo with the use of materials (e.g., polymers or natural scaffolds) to support the attachment, growth, and/or proliferation of cells that have some of the characteristics of native skeletal muscle. However, and particularly in cases where the magnitude of the injury or disease significantly exceeds the regenerative capacity of the remaining viable tissue (e.g., volumetric muscle loss resulting from traumatic injury), better therapeutic solutions are needed to create functional muscle tissue.

SUMMARY OF THE INVENTION

Provided herein are methods useful to promote the formation of functional clusters on a tissue, for example, motor endplates (MEPs) or a component thereof on skeletal muscle tissue. In some embodiments, promotion of a cluster of acetylcholine receptors on the muscle tissue promotes the muscle phenotype, such as inclusion of multinucleated myotubes, expression of mature muscle markers (e.g., myogenin, MHC, titin, etc.) prior to and after implantation of the tissue engineered construct, so that when re-innervation does occur in vivo, the tissue engineered implant can still function, and preferably function more optimally.

Also provided herein are scaffolds useful for growing cells thereon. In some embodiments, the scaffold includes one or more agents of interest at separate and discrete locations in or on the scaffold. In some embodiments, the scaffold includes beads (e.g., microbeads or nanobeads) therein or thereon, wherein said beads comprise an agent of interest. In some embodiments, the agent of interest is incorporated onto the beads though covalent coupling.

In some embodiments, the scaffold is a skeletal muscle cell scaffold or a cardiac muscle cell scaffold. In some embodiments, the agent of interest is agrin.

In some embodiments, the scaffold includes fibrin, collagen, agarose, cellulose, alginate, agarose, keratin, hydroxymethyl cellulose, or poly(hydroxyethylmethacrylate).

Also provided are methods of making a skeletal muscle implant, including providing a scaffold as described herein and seeding cells (e.g., muscle cells such as myoblast cells or satellite cells) onto said scaffold. In some embodiments, the methods also include isolating muscle cells from a donor tissue.

Further provided are methods of making a scaffold including beads therein or thereon, including one or more of the steps of: providing a material (e.g., a hydrogel) including beads, which beads include an agent of interest; applying the material onto a template (e.g., a fiber template); polymerizing the material around the template to form a polymerized material; and then, selectively dissolving the template to create hollow spaces (e.g., hollow tubes) within the polymerized material.

Still further provided are methods of culturing organized skeletal muscle tissue from precursor muscle cells (e.g., myoblast cells or satellite cells), including cyclically stretching and relaxing the muscle cells on a scaffold in vitro for a time sufficient to produce the organized skeletal muscle tissue; and further including agrin at separate and discrete locations in or on said scaffold, the agrin provided in an amount effective to promote the formation of aggregated acetylcholine receptors in the organized skeletal muscle adjacent to one or more of said separate and discrete locations.

In some embodiments, the separate and discrete locations are provided in a ratio of between 1:10 and 10:1, or at an approximately 1:1, 1:2, 1:3, 1:4, 1:5, 5:1, 4:1, 3:1, or 2:1 ratio, with respect to formed myotubes in the organized skeletal muscle tissue.

Also provided are methods of culturing organized skeletal muscle tissue from precursor muscle cells including cyclically stretching and relaxing said muscle cells seeded onto a fibrin or fibrinogen scaffold in vitro for a time sufficient to produce said organized skeletal muscle tissue, wherein the scaffold includes a plurality of channels aligned along a first axis.

Further provided are multi-layered skeletal muscle tissue produced by the methods as taught herein. In some embodiments, the tissue includes elongated multi-nucleated muscle fibers. In some embodiments, the tissue includes or expresses acetylcholine (ACh) receptors. In some embodiments, the tissue includes aggregated ACh receptors. In some embodiments, the tissue includes aggregated ACh receptors forming a pretzel shape characteristic of motor end plates. In some embodiments, the tissue includes aggregated ACh receptors which are at a ratio of 10:1 and 1:10, or between 5:1 and 1:5, or between 1:2 and 2:1, with respect to said elongated multi-nucleated muscle fibers. In some embodiments, the tissue is suturable.

Still further provided are methods of treating a skeletal muscle injury or defect in a subject in need thereof including grafting an engineered tissue as described herein into the subject in a treatment-effective configuration.

Also provided is an engineered tissue as taught herein for use in repairing a skeletal muscle injury or defect.

BRIEF DESCRIPTION OF THE DRAWINGS

FIG. 2 reports the effects of agrin-presenting beads on C2C12 cells cultured on fibrin hydrogels. Microparticle bead delivery vehicles without added agrin produce no response from treated cells (A). Physically adsorbing agrin to the bead surface allows for spatially targeted induction of a clustering response in membrane-bound acetylcholine receptors after 1 day of treatment at areas of contact between cells and bead delivery vehicles (B). Though agrin-adsorbed beads are ineffective at generating a clustering response after 3 days of treatment (data not shown), linking agrin to the microparticle surface using EDAC/sulfo-NHS covalent crosslinking chemistry allows for induction of clustering behavior at 5 days of treatment (C) or beyond. Dotted lines show approximate cell-seeded area in the plane of focus, and arrows indicate foci of acetylcholine receptor clustering. All areas of clustering occur where beads are present, indicating the importance of the agrin-presenting beads in promoting clustering behavior. Results also suggest that adsorption of agrin to bead surface is superior in short-term applications, while covalent crosslinking between agrin and the bead enables cell signaling in the long term.

FIG. 4 shows receptor clustering in myotube-like cell membranes in response to 5 days of treatment with agrin-delivering microparticles. Confocal imaging eliminates out-of-plane signal, producing an image of a very thin "slice" of tissue. Progressive slices can be used to show the evolution of signals across all three dimensions of a structure. Micrographs of fluorescent labeling using α-bungarotoxin beginning beneath microparticles (A), advancing vertically (B), and ending near the center of the microparticle vertical thickness (C) show that cells respond to agrin delivery via formation of AChR clusters (staining) at areas of microparticle contact. Dotted outlines depict locations of microparticles with agrin covalently linked to bead surface. As seen across the three sequential sub-images, clustering behavior is independent of bead orientation at area of contact, meaning a bead may equally signal a cell it is on top of, beside, or contacting at any oblique angle. Similarly, one agrin-delivering particle can signal multiple adjacent cells, indicating that production of a response in one cell does not meaningfully deplete the agrin-coupled bead's ability to impart its signal.

FIG. 5 illustrates the efficacy of myoblast-like cell seeding of patterned fibrin scaffolds. Scaffolds were fabricated via polymerization of fibrinogen in the presence of thrombin and calcium around a sacrificial pMMA template. The template was dissolved, leaving a porous network of hollow cylindrical channels within a macroscopic fibrin biomaterial. C2C12 cells were seeded statically by adding in suspension on top of the scaffold (from the left of the image), cultured for 1 day in growth medium, and differentiated toward a myotube-like phenotype for 10 further days. Low-magnification imaging of a sagittal scaffold section shows cells readily colonized the entire thickness of the scaffold (left to right of image) by migration during the growth and early differentiation phases as visualized by DAPI nuclear stain. Higher-magnification views near the top, middle, and bottom of the scaffold thickness reveal that myotube-like cells have fused within the scaffold and are expressing acetylcholine receptors (data not shown).

DETAILED DESCRIPTION OF PREFERRED EMBODIMENTS

Provided herein and further described below are compositions and methods useful for producing functional muscle tissue in vitro for implantation in vivo. The disclosures of all patent references cited herein are hereby incorporated by reference to the extent they are consistent with the disclosure set forth herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Implant" refers to a product configured to repair, augment or replace (at least a portion of) a natural tissue of a subject (e.g., for veterinary or medical (human) applications). The term "implantable" means the device can be inserted, embedded, grafted or otherwise chronically attached or placed on or in a patient. Implants include a support with or without having cells seeded thereon and/or subjected to bioconditioning according to some embodiments as described herein.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including prenatal, newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with or at risk for developing a disease (e.g., a musculoskeletal disease), injury, or other impairment or defect. Treating includes actions taken and actions refrained from being taken for the purpose of improving the condition of the patient (e.g., the relief of one or more symptoms), delay in the onset or progression of the disease, etc. Treatment includes that of any disease or injury associated with the loss or dysfunction of skeletal muscle, such as the treatment of volumetric muscle loss or congenital defects in the limbs or face, for which current treatments do not fully repair the defects. Other examples include, but are not limited to, the loss or denervation of skeletal muscle due to disease conditions such amyotrophic lateral sclerosis (ALS), post-polio syndrome, muscular dystrophy, etc.

In some embodiments, treating includes reconstructing skeletal muscle tissue (e.g., where such tissue has been damaged or lost by, e.g., injury or disease) by implanting an scaffold (e.g., an anisotrophic scaffold, with or without muscle cells) into a subject in need thereof. Scaffolds may be implanted, e.g., at or adjacent to the site of injury, and/or at another site in the body of a subject that would impart a benefit to the subject, as would be appreciated by one of skill in the art.

Muscle cells used to carry out the present invention may be isolated according to methods known in the art, and are preferably mammalian muscle cells, including, but not limited to, human, other primate such as monkey, baboon, pig, sheep, goat, horse, dog, rodent such as mouse, rat, etc. In general, such cells are skeletal muscle cells. Muscle cells of other species, including birds, fish, reptiles, and amphibians, as well as arthropods and/or invertebrate skeletal muscle may also be used, if so desired. In some embodiments, the cells are precursor cells, or cells that are capable of differentiating into mature, multinucleated muscle cells, under appropriate culture conditions and stimuli as described herein. Muscle precursor cells are known. See, e.g., U.S. Pat. No. 6,592,623.

In some embodiments, skeletal muscle progenitor cells isolated from muscle tissue are used. In some embodiments, stem cells are used, and may be optionally differentiated toward the skeletal muscle phenotype before and/or after seeding onto the scaffold. "Skeletal muscle cells" include, but are not limited to, myoblasts, satellite cells and myotubes.

"Myoblasts" are a type of muscle precursor cell that can fuse with each other and give rise to myotubes. Myoblasts are thought to arise from satellite cells and are normally closely associated with myofibers during the course of their life cycle in the vertebrate organism (Zammit et al., 2006; Journal of Histochemistry & Cytochemistry). If the myofiber is injured, the satellite cells become activated and give rise to myoblasts, which are capable of further dividing and repairing damaged muscle and/or forming new fibers. Typically, after muscle injuries myofibers become necrotic and are removed by macrophages (Hurme et al. (1991) Healing of skeletal muscle injury: an ultrastructural and immunohistochemical study, *Med. Sci Sports Exerc.* 23, 801-810). This induces proliferation and fusion of myoblasts as described above to form multinucleated and elongated myotubes, which self-assemble to form a more organized structure, namely muscle fibers (Campion (1984) The muscle satellite cell: a review, *Int. Rev. Cytol.* 87, 225-251). Myoblasts may be harvested from an appropriate donor and isolated by standard techniques.

"Myotubes" are elongated, multinucleated cells, normally formed by the fusion of myoblasts. Myotubes can develop into mature muscle fibers, which typically have peripherally-located nuclei and myofibrils in their cytoplasm (e.g., as found in mammals).

"Isolated" as used herein signifies that the cells are placed into conditions other than their natural environment. Tissue or cells are "harvested" when initially isolated from a subject, e.g., a primary explant. In one embodiment, cells may be isolated from a donor (e.g., living or cadaveric) or obtained from other cell sources. In one embodiment, cells may be obtained from the muscle.

Cells may be syngeneic (i.e., genetically identical or closely related, so as to minimize tissue transplant rejection), allogeneic (i.e., from a non-genetically identical member of the same species) or xenogeneic (i.e., from a member of a different species) with respect to the subject. Syngeneic cells include those that are autogeneic or autologous (i.e., from the patient to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a bioscaffold graft) using standard biopsy techniques known in the art.

Any suitable culture media can be used to grow cells in the present invention, including medias comprising serum and other undefined constituents, defined medias, or combinations thereof, such as RPMI, DMEM, etc.

The "primary culture" is the first culture to become established after seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express a certain protein or marker).

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other biological marker. Expression of certain proteins or other markers may be indicative of a certain phenotype, as known in the art.

"Scaffolds" on which cells may be seeded and grown to produce cultured tissue include any suitable support. See, e.g., U.S. Pat. Nos. 6,998,418; 6,485,723; 6,206,931; 6,051,750; and 5,573,784. Preferably, the scaffold is configured to support the attachment, proliferation and/or differentiation of cells thereon.

The scaffold may be formed from any suitable material, including, but not limited to, synthetic or natural polymers, other biopolymers, and combinations thereof. In some embodiments, scaffolds include collagen supports or decellularized tissue supports (e.g., obtained from smooth muscle or skeletal muscle, such as a decellularized mammalian (e.g., porcine) bladder such as bladder acellular matrix (BAM)). In some embodiments, scaffolds include a polymeric matrix (e.g., collagen, a hydrogel, etc.). In some embodiments, scaffolds include fibrin or fibrinogen.

The scaffold may be of any suitable configuration, but in some embodiments comprises, consists of, or consists essentially of a generally flat planar portion, such as a sheet. In other embodiments, the scaffold comprises, consists of, or consists essentially of a generally tubular configuration. The scaffold may be of any suitable thickness, but in some embodiments are at least 20, 30, 50 or 100 µm thick, up to 600, 800, or 1000 µm thick, or more. In some embodiments, scaffolds are 0.5 mm to 20 mm, or 1 mm to 15 mm, or 3 mm to 10 mm thick.

In some embodiments, scaffolds have sufficient mechanical integrity for skeletal muscle applications. In some embodiments, scaffolds have a tensile strength of from 10 kPa to 1000 kPa, or 50 kPa to 500 kPa, or 100 kPa to 300 kPa. In some embodiments, scaffolds have a tensile strength of at least 10, 50, 100 or 300 kPa.

In some embodiments, scaffolds have a Young's modulus of from 10 kPa to 5000 kPa, or from 100 kPa to 2500 kPa, or from 500 kPa to 1000 kPa. In some embodiments, scaffolds (e.g., fibrin scaffolds) have a Young's modulus of from 100 kPa to 350 kPa. The Young's modulus for scaffolds fabricated by the techniques described herein can be tailored to mimic the native modulus of muscle cells and tissue, with scaffolds of higher and lower moduli readily fabricated, allowing for the use of materials that have physiologically-relevant mechanical properties and/or that can withstand the rigors of various in vitro and in vivo environments.

In some embodiments, scaffolds have mechanical integrity sufficient to withstand the mechanical stimulation (e.g., cyclic loading) in a bioreactor to produce the desired skeletal muscle tissues. For example, in some embodiments scaffolds are able to withstand the cell seeding and preferred bioreactor pre-conditioning protocols described for at least 5, 10, 15, 17 or 20 days or more, in PCT application no. PCT/US2011/047600, filed Aug. 12, 2011, and published as WO 2012/021814, to Christ et al., which is incorporated by reference herein in its entirety.

In some embodiments, the scaffold is conditioned in a bioreactor to support the growth and maturation of cells. In other embodiments, the scaffold is directly implanted in vivo.

In some embodiments, scaffolds as provided herein are useful for the localized delivery of agents of interest. For example, in some embodiments, the scaffold may include components that are actively presented to cells to promote functional formation and/or maintain phenotypic characteristics of cells in vitro and/or following implantation.

For example, agents may be used that promote the formation of motor endplates (MEPs) on skeletal muscle constructs, which can improve the maintenance of phenotypic characteristics of skeletal muscle cells. Without wishing to be bound by theory, it is thought that the promotion of MEP formation in skeletal muscle constructs will promote the maintenance of an innervated muscle phenotype prior to and/or after implantation of the tissue engineered construct, so that when re-innervation by the native tissues does occur, the tissue-engineered implant will retain at least a portion of this functionality. For example, it is expected that this will increase the rate and magnitude of functional muscle recovery seen with the implanted constructs. In some embodiments, the rate of recovery is from 2, 3, or 4 to 6, 8 or 10 weeks. In some embodiments, the magnitude of recovery is at least 30, 40, 50, 60, 70, 80 or 90% of the original force generation. In some embodiments, the magnitude of recovery is from 30 to 90%, or 40 to 80%, or 50 to 75% the original force generation.

In addition to the use of agrin to promote MEPs in skeletal muscle constructs, other agents may be used to promote desired phenotypes in other cell types, including, but not limited to, smooth muscle cells, endothelial cells, nerve cells, Schwann cells, bone cells, etc. By incorporating chemical cues through incorporation into scaffolds (e.g., muscle scaffold, blood vessel scaffolds, etc.) or by the direct presentation (e.g., by injection) of the agent, more functional phenotypes can be obtained or maintained for regenerative medicine/tissue engineering applications. For example, an angiogenic compound such as VEGF can be seeded on or carried by the scaffold to facilitate the formation of vascular cells or vasculature in the tissue.

In some embodiments, scaffolds provide localized delivery of agents of interest by incorporating on or into beads. "Beads" as uses herein refers to discrete particles of any geometrical shape (spheres, rectangles, cones, etc.), typically on the micro ($10^{-6}$) or nano ($10^{-9}$) scale (microbeads or nanobeads). In some embodiments, beads include or are made of materials such as polystyrene or other polymeric material such as poly(ethylene), poly(lactic acid), poly(glycolic acid), or poly(lactic-co-glycolic acid); or gold, silver, iron oxide, etc. The particles may include one or more agents of interest (e.g., growth or development factors, such as agrin, acetylcholine, etc.) useful to promote phenotypes of interest in the engineered tissue. In some embodiments, beads have an average diameter of less than 0.1 µm. In other embodiments, beads have an average diameter of more than 1 mm. In some embodiments, beads have an average diameter of 0.1 µm to 1 mm, or 1 µm to 0.5 mm, or 10 µm to 100 µm.

For example, in some embodiments, the local delivery of agrin to skeletal muscle tissue may promote the formation of acetylcholine receptor clustering or other components involved in the formation of motor endplates and/or neuromuscular junctions. Other agents that may be used include, but are not limited to, heparin-binding growth-associated molecule (HB-GAM), muscarine, acetylcholine receptor antibodies, carbachol, and nicotine. Biglycan or other agents that stabilize dystrophin-associated protein complexes may also be used. See U.S. Patent Application Publication No. 2011/0183910 to Fallon et al.

Any suitable method to couple the agent of interest to the beads may be used. For example, the agent may be adsorbed or covalently coupled to the beads through various chemistries including EDAC/NHS (for carboxyl-amine coupling) or maleimide chemistry (for coupling to sulfhydryl groups). The beads can be placed on or within the scaffold to promote the formation of discrete functional clusters on the tissue. In some embodiments, beads are provided on or in the scaffold at a density of from $10^3$, $10^4$, or $10^5$ per cm$^3$, to $10^8$, $10^9$, $10^{10}$ or $2\times10^{10}$ per cm$^3$.

In some embodiments, beads comprising an agent may be directly injected at a site of interest. For example, beads comprising agrin (e.g., provided in a carrier such as a hydrogel) may be injected into a site of denervation or muscle motor loss to maintain phenotype in vivo.

In some embodiments, the scaffold contains aligned or substantially aligned hollow conduit channels (e.g., along an axis of the support), or other porous architecture that supports the infiltration of cells (e.g., myoblasts, myotubes, etc.) and/or sub-cellular components. These scaffolds may be fabricated by a templating approach or other methods to achieve the preferred architecture.

In some embodiments, the scaffold is a three-dimensional fibrin or fibrinogen scaffold. Fibrinogen is a soluble plasma glycoprotein that can be converted by thrombin into fibrin, such as normally occurs during blood coagulation. These scaffolds include those made by forming the scaffold around a dissolvable core to mold the inner channels. For example, the fibrin or fibrinogen scaffold may be formed around poly(methyl-methacrylate) (pMMA) beads, after which the beads are dissolved with acetone to form an interconnected microporous network. See, e.g., Linnes et al., Biomaterials 28 (2007) 5298-5306. In other embodiments, scaffolds may be formed around polymer rods. See, e.g., Flynn et al., Biomaterials (2003) 4265-4272; Stokols et al., Tissue Engineering 12(10) (2006) 2777-2787.

In some embodiments, the channels may be formed from a modification of the production of fibrinogen-based porous scaffolds with polymer (e.g., 100 kDa pMMA, or poly(tetrafluoroethylene)) fibers are extruded on a piston extrusion system. Fiber diameter may be varied based on the extrusion temperature and rate of uptake on collection godets. The fibers may then be packed into a desired geometry.

In some embodiments, any hydrogel material and fiber combination can be used, so long as an appropriate solvent can be used to selectively remove/dissolved the fibers. Other polymeric materials that may be used as the sacrificial template fibers include, but are not limited to, polystyrene, poly(ethylene glycol), poly(tetrafluoroethylene) poly(vinyl alcohol), poly(lactic acid), poly(glycolic acid), poly(lactic-co-glycolic acid), poly(caprolactone), and alginate.

Other hydrogel materials that may be used include, but are not limited to, collagen, agarose, cellulose (and modifications thereof), alginate, agarose, keratin, hydroxymethyl cellulose, and poly(hydroxyethylmethacrylate). It is preferable in some embodiments that the template and hydrogel materials have different solubilities in order to promote selective (sacrificial) removal of the template fibers. In some embodiments, beads are included in the hydrogel phase.

Figure 1A:
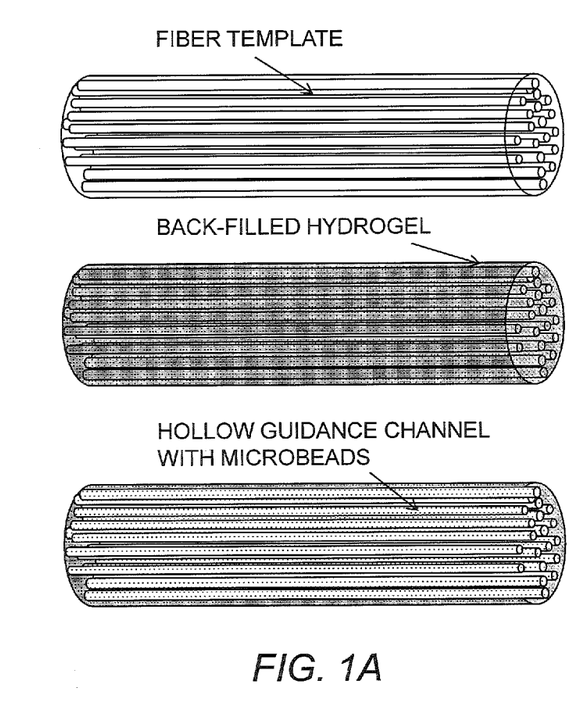
FIG. 1A-1B provides a schematic example of the formation of a fibrin hydrogel scaffold (A), which can be (B) seeded with cells and/or containing polystyrene beads capable of providing acetylcholine receptor agonist stimulation through agonist presentation (triangles).
Figure 1B:
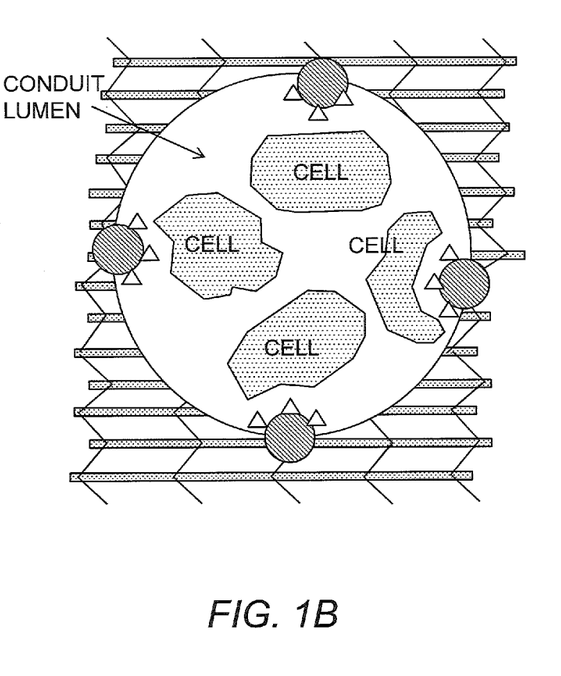

A schematic representation of a fabrication process for supports according to some embodiments is given in FIG. 1. First, a fiber template is formed (A). The fiber may be a polymer, e.g., pMMA. The fibers may be formed by different processes and formed to desired diameters (e.g., by melt extrusion). A hydrogel material (e.g., fibrinogen) is then backfilled into the template (e.g., by centrifugation or positive or negative pressure). The hydrogel material may then be polymerized (e.g., fibrinogen may be polymerized to fibrin with thrombin and calcium). The polymer mold or template may then be selectively dissolved by a solvent (e.g., pMMA may be dissolved by acetone), creating, for example, hollow tubes which may serve as aligned conduits. Locally-stimulating beads (circles) that may include an agent such as agrin (triangles) may be incorporated into the construct (B). These may be included in the hydrogel during the backfill process or may be incorporated after the support is formed, e.g., through absorption, covalent crosslinking, etc.

In some embodiments, hollow channels in the scaffold have a diameter or average diameter of from 0.1, 1, 5, or 10 μm to 1, 5 or 10 millimeters, or 100, 500, 1000 or 5000 millimeters. Other geometries may also be used, as desired. For example, scaffolds may be provided with substantially spherical pores. See, e.g., U.S. Pat. No. 7,972,628 to Ratner et al.

In some embodiments, cells are seeded onto (e.g., onto the surface) or into (e.g., within the volume of) a scaffold. Cell seeding may be accomplished statically, e.g. by adding a suspension of cells in appropriate culture medium to one or more faces of the scaffold, after which cells settle onto and/or infiltrate the scaffold via gravity and/or native cellular motility. Cell seeding may also be accomplished dynamically using a bioreactor, which may act to guide or push/pull cells into the scaffold, for example by agitation or fluid flow of the cell suspension around and/or through the bulk of a scaffold and/or its porous architecture.

In some embodiments, scaffolds with beads and/or cells are subjected to bioreactor pre-conditioning to facilitate maturation of myoblasts to form myotubes and other markers of mature skeletal muscle cells. See, e.g., patent application publication no. 2006/0239981 to Yoo et al.; and PCT patent application serial no. PCT/US2011/047600, filed Aug. 12, 2011, to Christ et al., which are each incorporated by reference herein in their entireties. Any suitable bioreactor device can be used, such as those described in the aforementioned patent applications.

In some embodiments, a "mold" is provided which is configured to fit within the bioreactor and also designed to confine a cell suspension on top of and/or within one or more of the scaffolds and/or scaffolds seeded with cells. The mold may be made of a light-weight material (with a total weight, e.g., of 1-5 grams) and preferably does not significantly damage the underlying cellular structures when placed onto the scaffold and/or scaffold seeded with cells.

Multiple cell seeding protocols (i.e., more than just this one additional one, to include additional increases in bioreactor preconditioning) may also be performed. As an example, if each additional cell seeding is carried out during a time of between 3 and 4 days, the number of cell seedings according to some embodiments may be 2, 3, 4, 5, 6, 7, or 8 or more.

The length of stretching of the scaffold may be to a dimension at least 5% greater in length than the static position, and in some embodiments preferably not greater that 15%, and the relaxing may comprise retracting the scaffold to a dimension not greater in length than the static position. In some embodiments the "static position" may be intermediate between the stretched and relaxed position, and in such cases the relaxing may comprise retracting the scaffold to a dimension at least 5% lesser in length than the static position.

The first time period, during which the stretching and relaxing occurs, may be of any suitable length, for example from 2 or 3 minutes up to 10, 20 or 30 minutes in duration or more. The step of cyclically stretching and relaxing is typically carried out at least two or three times during the first time period (e.g., from 2, 3 or 4 times, up to 10 or 20 times).

The second time period during which the scaffold is maintained in a static position, may be of any suitable duration. In some embodiments the second time period is shorter than the first time period, and may be from 1 or 2 minutes in duration up to 10 or 20 minutes in duration. In other embodiments the second time period is longer than the first time period, and may be from 10 or 20 minutes in duration up to 40, 60 or 90 minutes in duration, or more. In some embodiments, such as where the first time period contains comparatively long intervals between stretching and relaxing, the need for a second time period may be obviated altogether.

In some embodiments, the scaffold is cyclically stretched and relaxed during a first "active" time period to a dimension of 10% greater and lesser in length than the static dimension at a rate of 3 cycles per minute for a total of five minutes, followed by a 25 minute "rest" second time period, continuously for 1 to 3 weeks of in vitro culture. In some embodiments, this protocol may result in an increase in the number of multinucleated cells, thicker myotube width, better cellular alignment, etc., in the construct. In some embodiments, this protocol may result in an increase in the number of multinucleated cells, thicker myotube width, better cellular alignment, etc., in the construct (by, e.g., 10, 20, 50, 80 or 100%).

In some embodiments, the construct (scaffold plus cells) is characterized by containing one or more neuromuscular junction features, particularly post-synaptic features such as the expression of acetylcholine (ACh) receptors, and in some embodiments the ACh receptors are aggregated. In some embodiments, aggregated ACh receptors may include those which have or approximate the characteristic pretzel shape of a motor endplate in innervated mature fibers in vivo.

In native tissue, the neuromuscular junction (NMJ), or nerve-muscle synapse, include the pre- and post-synaptic specializations of the motor neuron and muscle, respectively, the intervening synaptic basal lamina, and the specialized Schwann cell cap (Salpeter, et al (1987) The Vertebrate Neuromuscular Junction. New York, Alan R. Liss.). The presynaptic apparatus is typically marked by ordered arrays of synaptic vesicles, a subset of which are poised to fuse with the plasma membrane at the active zones, and release acetylcholine that is recognized by acetylcholine receptors (AChRs) on the muscle, and ultimately results in electrical activation and contraction of the muscle (Heuser, et al (1981) J. Cell Biol. 88: 564). Immediately across the 50 nm synaptic cleft from these zones are the crests of the postjunctional folds. These crests bristle with Acetylcholine receptors (AChRs), which can reach densities of >10,000 molecules/$\mu m^2$ (Huh et al. (2002) Mol. Neurobiol. 25: 79). The localized and tightly regulated secretion of acetylcholine into the narrow synaptic cleft, coupled with the high AChR density in the postsynaptic membrane, ensures rapid and reliable synaptic transmission between neuron and muscle. Perturbations of these specializations, such as the decrease in the number of functional AChRs seen in myasthenia gravis, can lead to debilitating and often fatal clinical outcomes (Oosterhuis, et al (1992) Neurology & Neurosurgery 5: 638).

In some embodiments, beads comprising an agent of interest is provided on the scaffold such that a proper stoichiometry, or ratio of beads:cells (i.e., number of beads per cell) is achieved. In some embodiments, the ratio of beads to cells is 1:100 to 100:1, or 1:50 to 50:1, or 1:20 to 20:1, or 1:15 to 15:1, 1:10 to 10:1, or 1:8 to 8:1, or 1:5 to 5:1, or 1:4 to 4:1, or 1:3 to 3:1, or 1:2 to 2:1, or approximately 1:1, 1:2, 1:3, 1:4, 1:5, 5:1, 4:1, 3:1, or 2:1.

In the case of skeletal muscle, in some embodiments it may be optimal to provide beads comprising an agent that promotes the formation of neuromuscular junction features, such as agrin, in an approximately 1:1, 1:2, 1:3, 3:1, or 2:1 ratio of beads to cells to promote the formation of approximately one point of innervation per cell. This may be preferable in some embodiments to reduce colliding waves of excitation that may occur when there are multiple sites of innervations per cell (e.g., fused cells formed after bioreactor conditioning). The density of the beads on or in the scaffold may be altered, as desired, to obtain the stoichiometry of choice.

In some embodiments, myotubes have a length of about 300 to 1500 µm and a diameter of about 20 to 30 µm. These sizes may be used in some embodiments to calculate the concentration/distribution of beads in or on the scaffold in order to obtain the desired stoichiometry.

Skeletal muscle tissue produced as described herein may be used in vitro to examine the pharmacological or toxicological properties of compounds of interest (e.g., by adding the compound of interest to a culture medium in which the tissue is immersed, and examining the histological or mechanical properties of the tissue as compared to a control tissue).

Skeletal muscle tissue constructs produced by the methods of the present invention are in some embodiments "suturable" in that they have sufficient structural integrity to be surgically sutured or otherwise fastened at either end when implanted, and thereafter are capable of developing tension upon contraction.

Skeletal muscle tissue constructs produced as described herein may be used for the reconstruction of damaged tissue in a patient, e.g., a patient with a traumatic injury of an arm or leg. Such tissue may be formed on a support (which is also implanted) or removed from the support prior to implantation into the subject. The skeletal muscle tissue may be implanted to "build" soft tissue (e.g., at the interface between an amputated limb and a prosthetic device) or to reconstruct (partially or totally) a damaged muscle (e.g., a muscle of the face, hand, foot, arm, leg, back or trunk). The skeletal muscle tissue in some embodiments has, in some embodiments, a size or volume of at least 1, 2, or 3 or more cubic centimeters (not counting the volume of the support if present), and/or a length of 1 cm to 50 cm, to provide sufficient tissue mass for implantation in a patient (e.g., in association with an existing muscle of the patient) and reconstruction of a skeletal muscle involved in, for example, movement of fingers.

For allogenic transplant into a patient, tissue constructs as described herein may be matched or tissue-typed in accordance with known techniques, and/or the subject may be administered immune suppressive agents to combat tissue transplant rejection, also in accordance with known techniques.

The present invention is explained in greater detail in the following non-limiting Examples.

EXAMPLES

Example 1. Expression of Acetylcholine Receptors

During the characterization of tissue engineered muscle repair construct (TEMR) morphology following bioreactor preconditioning, it was discovered that multinucleated cells of TEMR constructs expressed acetylcholine (ACh) receptors and, in rare cases, exhibited aggregation of these receptors. Interestingly, the aggregation of ACh receptors in one construct is beginning to exhibit the characteristic pretzel shape of a motor endplate in mature fibers. These findings are indicative of mature TEMR constructs that produce clinically relevant force, as innervation of implanted TEMR constructs is thought to promote functional restoration of traumatically injured muscle tissue, and it is now known that these cells 1) express ACh receptors and 2) have the capacity to develop a motor endplate.

Example 2. Agrin-Stimulated Acetylcholine Receptor Clustering

For proof-of-concept studies on the ability to achieve clustering of acetylcholine receptors via stimulation by agrin, a C2C12 mouse myoblast cell line was used. A 2-dimensional version of the scaffolds described above was also used to allow histological evaluation.

C2C12 cells were seeded on 2-dimensional fibrin hydrogels for 4-10 days. Separately, agrin was coated onto or covalently immobilized on the surface of polystyrene beads. At 3-6 days of C2C12 cell culture, the agrin-coated beads were placed onto the cells for 24 hours or more. Cells were then stained for alpha-bungarotoxin, a marker of acetylcholine receptor clustering.

Figure 2:
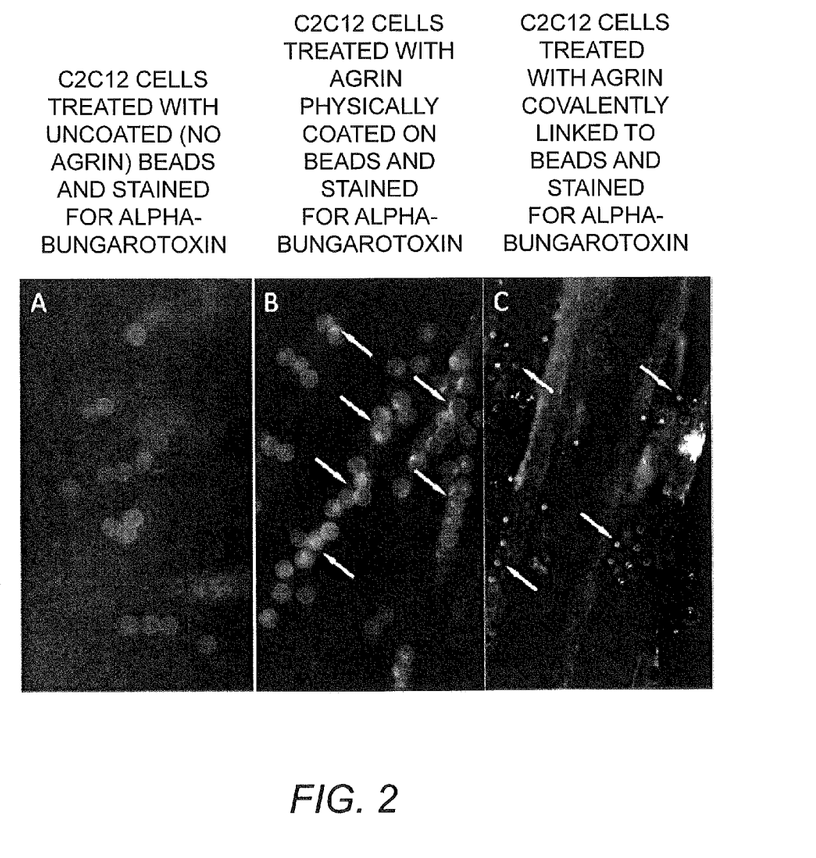

Agrin-coated beads on C2C12 cells cultured on fibrin hydrogels resulted in areas of clustering (FIG. 2). All areas of clustering occurred where beads were present, indicating that the agrin-coated beads promoted clustering behavior. Physical adsorption of agrin onto beads was shown to be superior for short-term signaling of cells (e.g., 1 or 2 days), while covalent immobilization enabled agrin delivery over longer time periods (e.g., 5 or more days). A higher magnification image confirmed that acetylcholine receptor clustering occurs only where beads are located (not shown).

Figure 3A:
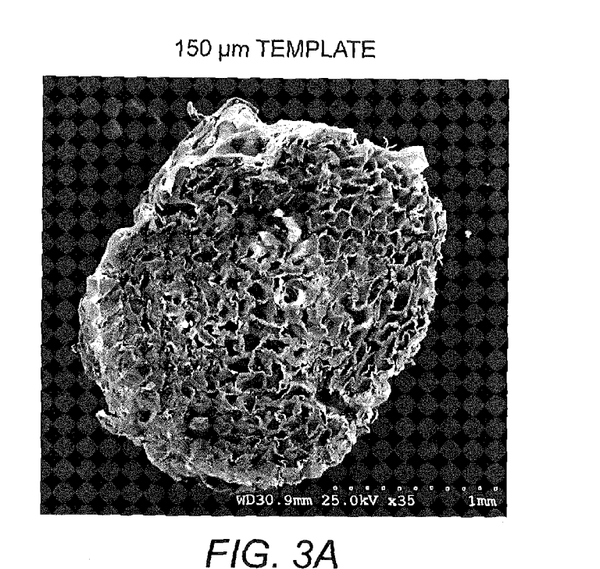
FIG. 3A-3B shows scanning electron microscope (SEM) images of scaffolds fabricated from pMMA templates and fibrin for nerve applications with a 105 μm template.
Figure 3B:
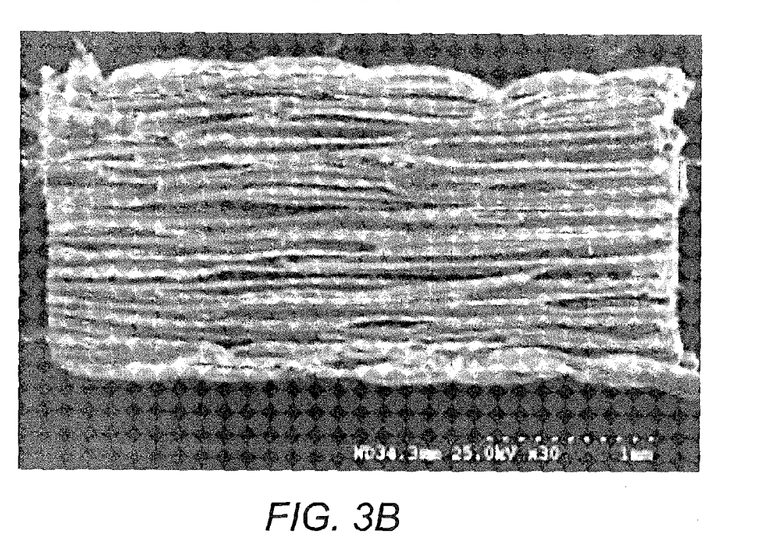

FIG. 3A-3B show scanning electron microscope (SEM) images of scaffolds fabricated from pMMA templates and fibrin for nerve applications with a 105 µm template.

Figure 4:
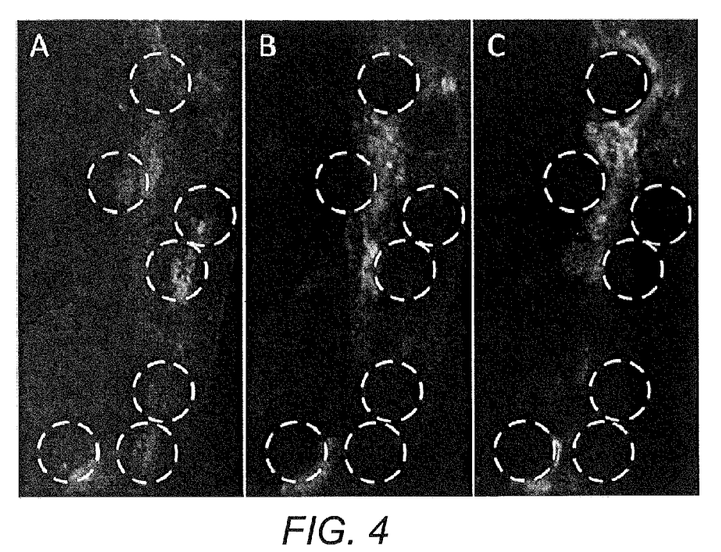

Clustering behavior was verified at areas of contact between cells and beads covalently linked to agrin using confocal microscopy (FIG. 4). Moreover, the unique ability of confocal microscopy to isolate signals in a vertical direction demonstrated independence of bead positioning relative to the cell for the purposes of clustering induced, as well as the ability of an agrin-delivering bead to signal multiple adjacent cells.

Example 3. Incorporation of Agrin-Coated Beads Into Scaffolds

Figure 5:
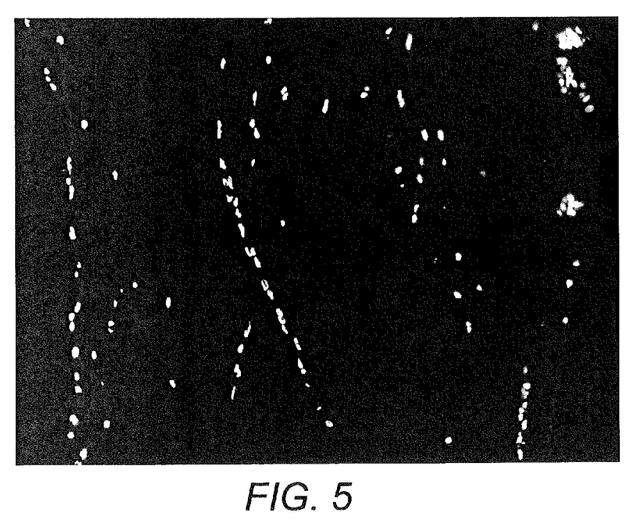

Agrin-coated beads are incorporated into 2-D hydrogels and the 3-D scaffolds described above (fabricated using a poly(tetrafluoroethylene) tubular or rectangular mold), myoblasts are seeded onto the formed 3-D scaffolds, and studies similar to those described above in Example 2 are conducted to determine the efficacy of cell seeding in three dimensions as well as the level of acetylcholine receptor clustering achieved when beads are part of the scaffold material. A rectangular, 3-D, patterned fibrin scaffold was seeded by static addition of a cell suspension and subsequent infiltration. As shown in FIG. 5, C2C12 cells substantially infiltrated the full thickness of the porous architecture via native cell motility, demonstrating the suitability of both the fibrin biomaterial and the sacrificial patterning process to myoblast-like cell seeding.

Furthermore, microscopy revealed that the seeded myotube-like cells fused within the scaffold and expressed acetylcholine receptors (data not shown).

The foregoing is illustrative of the present invention, and is not to be construed as limiting thereof. The invention is defined by the following claims, with equivalents of the claims to be included therein.

That which is claimed is:

1. A method of culturing organized skeletal muscle tissue from precursor muscle cells, comprising cyclically stretching and relaxing said muscle cells on a scaffold in vitro for a time sufficient to produce said organized skeletal muscle tissue, and further comprising:
including agrin at separate and discrete locations in or on said scaffold, said agrin provided in an amount effective to promote the formation of aggregated acetylcholine receptors in said organized skeletal muscle adjacent to one or more of said separate and discrete locations.

2. The method of claim 1, wherein said scaffold comprises fibrin, collagen, agarose, cellulose, alginate, agarose, keratin, hydroxymethyl cellulose, or poly(hydroxyethylmethacrylate).

3. The method of claim 1, wherein said precursor muscle cells are myoblast cells or satellite cells.

4. The method of claim 1, further comprising the step of isolating precursor muscle cells from a donor tissue.

5. The method of claim 1, wherein said scaffold further comprises one or more agents selected from: heparin-binding growth-associated molecule (HB-GAM), muscarine, acetylcholine receptor antibodies, carbachol, and nicotine.

6. The method of claim 1, wherein said tissue is suturable.

7. The method of claim 1, wherein said step of including agrin is carried out by including beads in or on said scaffold, with said beads comprising said agrin.

8. The method of claim 7, wherein said beads are microbeads.

9. The method of claim 7, wherein said separate and discrete locations are provided at an approximately 1:1, 1:2, 1:3, 1:4, 1:5, 5:1, 4:1, 3:1, or 2:1 ratio with respect to formed myotubes in said organized skeletal muscle tissue.

10. The method of claim 7, wherein said beads comprises polystyrene, poly(ethylene), poly(lactic acid), poly(glycolic acid), or poly(lactic-co-glycol acid).

11. The method of claim 7, wherein said beads comprise gold, silver, or iron oxide.

12. The method of claim 7, wherein said agrin is incorporated onto said beads though covalent coupling.

* * * * *